United States Patent
Akui et al.

(10) Patent No.: US 8,932,209 B2
(45) Date of Patent: Jan. 13, 2015

(54) SCANNING ENDOSCOPIC DEVICE AND METHOD OF DECREASING DIRECTIVITY OF BEAM LIGHT IN SCANNING ENDOSCOPIC DEVICE

(71) Applicant: Olympus Medical Systems Corp., Tokyo (JP)

(72) Inventors: Nobuaki Akui, Hino (JP); Yuji Sakai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/024,245

(22) Filed: Sep. 11, 2013

(65) Prior Publication Data

US 2014/0073950 A1 Mar. 13, 2014

Related U.S. Application Data

(63) Continuation of application No. PCT/JP2013/059282, filed on Mar. 28, 2013.

(30) Foreign Application Priority Data

May 31, 2012 (JP) .................................. 2012-124894

(51) Int. Cl.
| | | |
|---|---|---|
| *A61B 1/07* | (2006.01) | |
| *A61B 5/00* | (2006.01) | |
| A61B 1/00 | (2006.01) | |
| *G02B 23/24* | (2006.01) | |
| *G02B 23/26* | (2006.01) | |
| *G02B 26/10* | (2006.01) | |
| *A61B 1/04* | (2006.01) | |
| *A61B 1/06* | (2006.01) | |

(52) U.S. Cl.
CPC ........... *A61B 5/0062* (2013.01); *A61B 1/00172* (2013.01); *G02B 23/2423* (2013.01); CPC .... *G02B23/2469* (2013.01); *G02B 23/26* (2013.01); *G02B 26/103* (2013.01); *A61B 1/00009* (2013.01); *A61B 1/0002* (2013.01); *A61B 1/00032* (2013.01); *A61B 1/00045* (2013.01); *A61B 1/04* (2013.01); *A61B 1/0646* (2013.01); *A61B 1/07* (2013.01); *A61B 5/0084* (2013.01); *A61B 1/00096* (2013.01); *A61B 1/0017* (2013.01); *A61B 1/0011* (2013.01)
USPC ............................ 600/182; 600/129; 600/173

(58) Field of Classification Search
CPC .... A61B 1/00172; A61B 1/0017; A61B 1/07; A61B 5/0066; A61B 5/0068; G01Q 10/045
USPC .......... 600/182, 173, 129, 130, 478; 385/118; 359/196.1, 202.1; 250/227.26; 348/197
See application file for complete search history.

(56) References Cited

U.S. PATENT DOCUMENTS 6,754,518 B1   6/2004  Lloyd et al.
7,526,167 B1 * 4/2009  Minelly ....................... 385/126

(Continued)

FOREIGN PATENT DOCUMENTS

JP    A-62-138822    6/1987
JP    A-10-121333    5/1998

(Continued)

OTHER PUBLICATIONS

International Search Report issued in International Patent Application No. PCT/JP2013/059282 mailed May 7, 2013 (with translation).
Office Action issued in Japanese Patent Application No. 2013-540171 mailed Oct. 22, 2013 (with translation).

*Primary Examiner* — John P Leubecker
(74) *Attorney, Agent, or Firm* — Oliff PLC

(57) ABSTRACT

A scanning endoscopic device includes an optical fiber allowing irradiation light guided from a proximal side fiber portion to a distal side fiber portion to exit from a distal end thereof, and an actuator section placed to a distal direction side of the proximal fiber portion. The scanning endoscopic device includes a light absorbing section absorbing beam light having directivity in one direction, and the light absorbing section includes a black filling member filling a space between the proximal side fiber portion and an outer envelope tube in radial directions. The device further includes a light scattering section provided between the proximal side fiber portion and the outer envelope tube in the radial directions to scatter the beam of light.

6 Claims, 9 Drawing Sheets

(56) References Cited

U.S. PATENT DOCUMENTS

| | | | |
|---|---|---|---|
| 8,503,054 B2* | 8/2013 | Friese | 359/202.1 |
| 8,537,203 B2* | 9/2013 | Seibel et al. | 348/45 |
| 2007/0058230 A1* | 3/2007 | Blug et al. | 359/196 |
| 2009/0028407 A1 | 1/2009 | Seibel et al. | |
| 2010/0177368 A1 | 7/2010 | Kobayashi | |
| 2011/0085154 A1* | 4/2011 | Schwanke | 356/4.01 |
| 2013/0271771 A1* | 10/2013 | Sasaoka | 356/477 |
| 2014/0064684 A1* | 3/2014 | Sasaoka | 385/123 |

FOREIGN PATENT DOCUMENTS

| | | |
|---|---|---|
| JP | A-2002-500767 | 1/2002 |
| JP | A-2003-535659 | 12/2003 |
| JP | A-2008-100057 | 5/2008 |
| JP | A-2009-516568 | 4/2009 |
| JP | A-2010-162089 | 7/2010 |
| JP | A-2010-284261 | 12/2010 |
| JP | A-2011-217836 | 11/2011 |
| JP | A-2012-364 | 1/2012 |

* cited by examiner

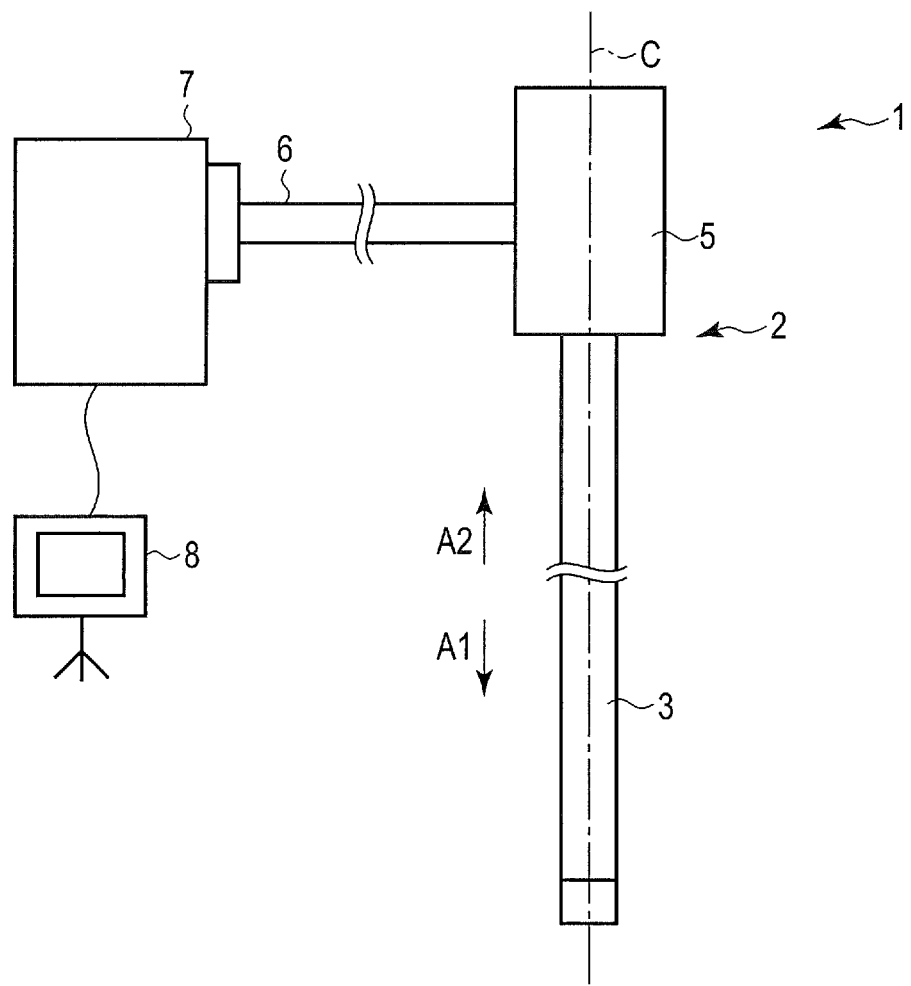
F I G. 1

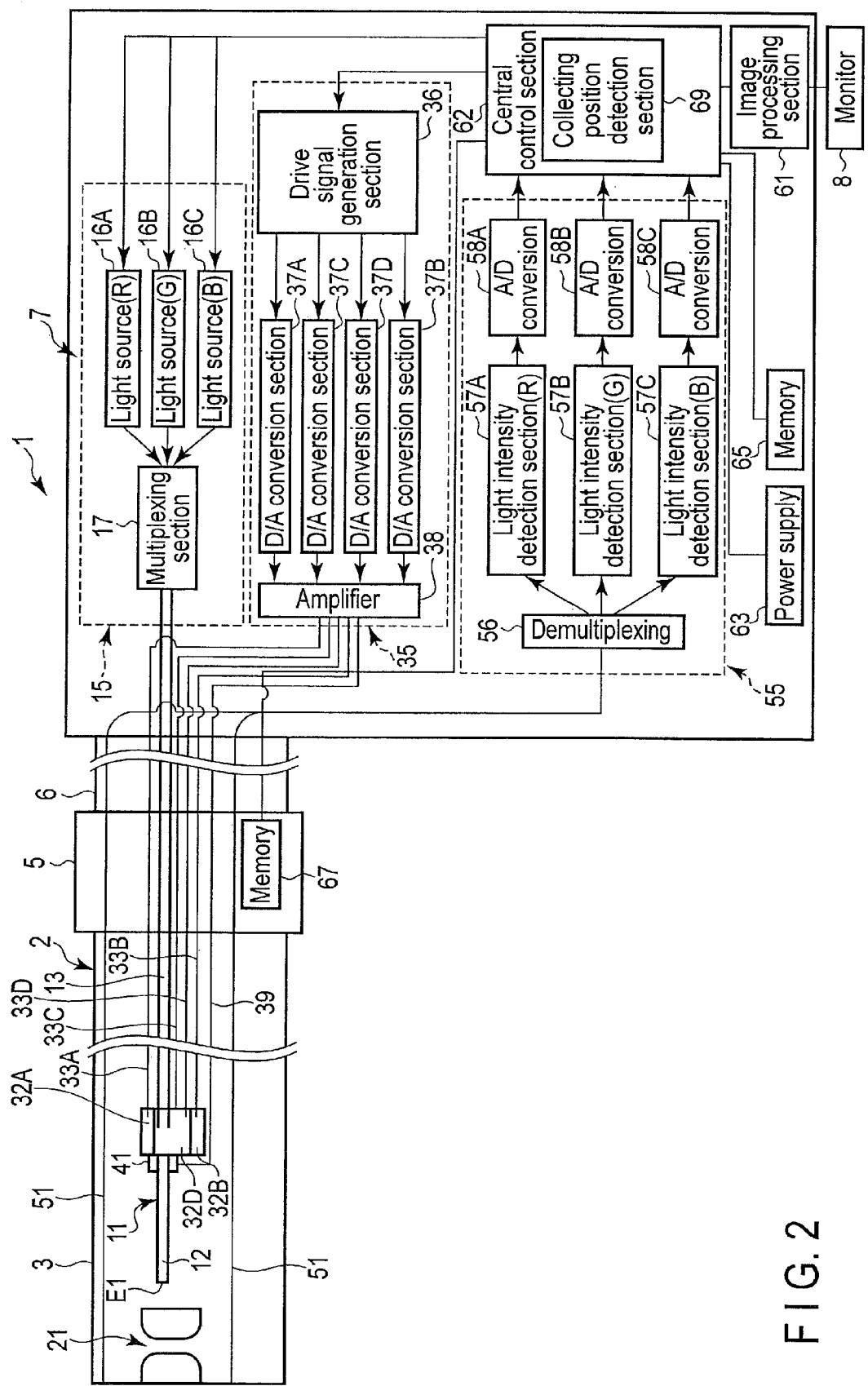
F I G. 2

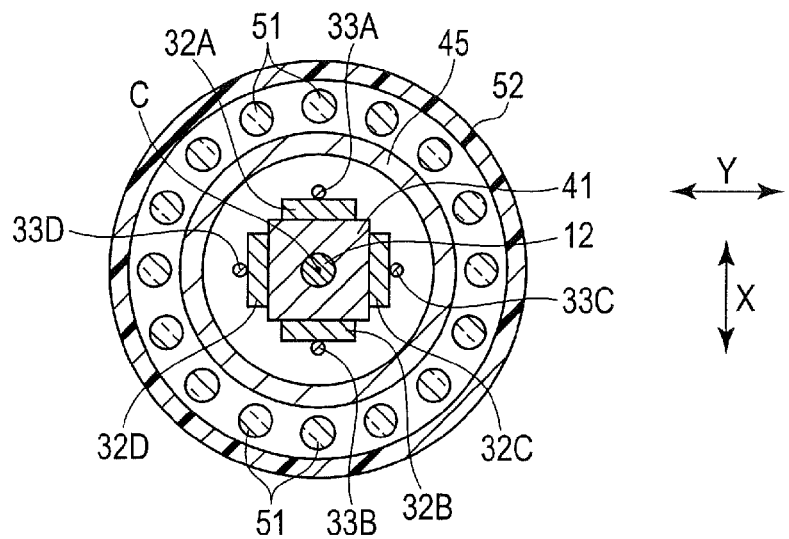
F I G. 5
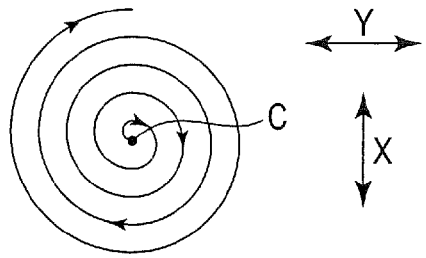
F I G. 6
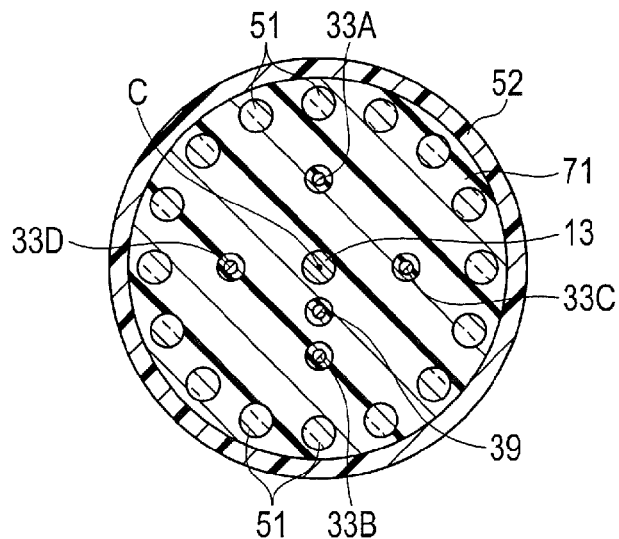
F I G. 7

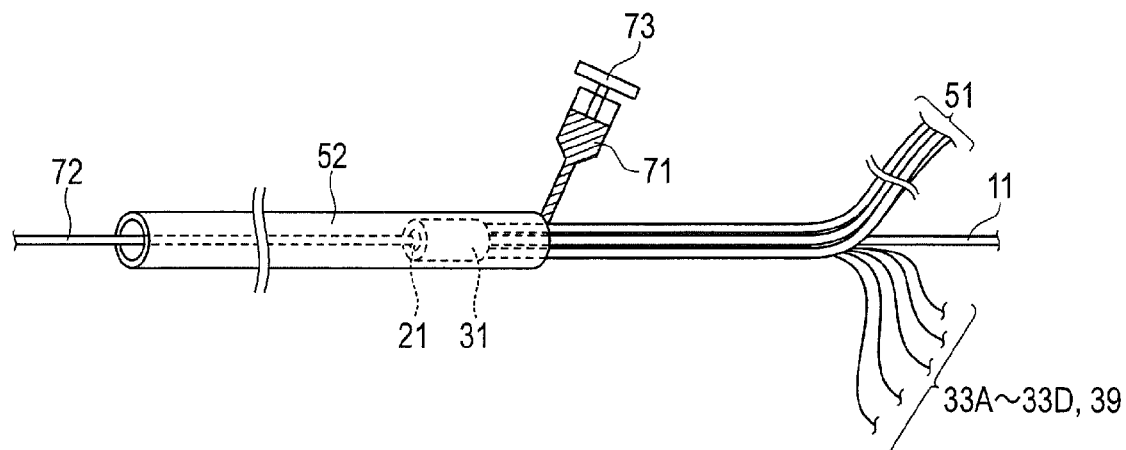
F I G. 8
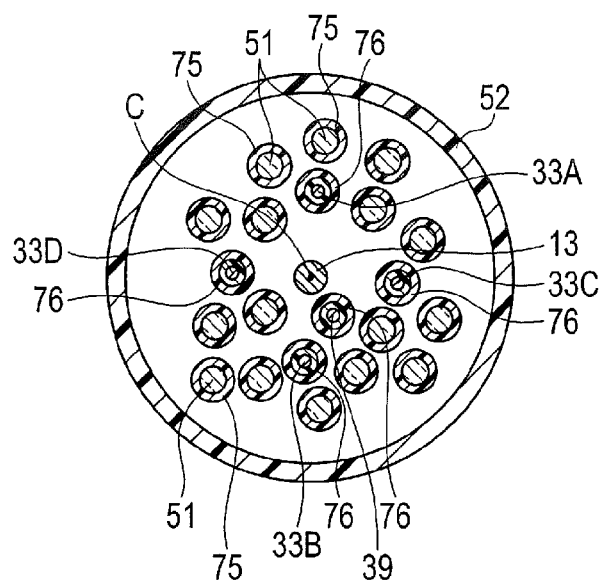
F I G. 9
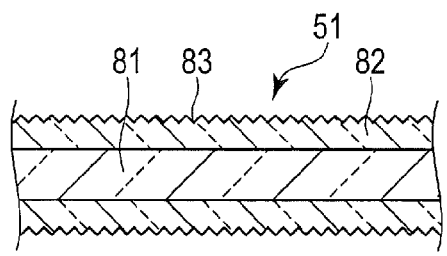
F I G. 10

SCANNING ENDOSCOPIC DEVICE AND METHOD OF DECREASING DIRECTIVITY OF BEAM LIGHT IN SCANNING ENDOSCOPIC DEVICE

CROSS-REFERENCE TO RELATED APPLICATIONS

This is a Continuation Application of PCT Application No. PCT/JP2013/059282, filed Mar. 28, 2013 and based upon and claiming the benefit of priority from prior Japanese Patent Application No. 2012-124894, filed May 31, 2012, the entire contents of which are incorporated herein by reference.

BACKGROUND OF THE INVENTION

1. Field of the Invention

The present invention relates to a scanning endoscopic device configured to generate an image of a subject by scanning the subject. Further, the present invention relates to a method of decreasing a directivity of beam light in the scanning endoscopic device.

2. Description of the Related Art

Jpn. PCT National Publication No. 2003-535659 discloses a scanning endoscopic device configured to generate an image of a subject by scanning the subject. In this scanning endoscopic device, irradiation light guided (led) from a light generation section exits from a distal end of an optical fiber, and the exiting irradiation light is collected (condensed) on the subject by a lens optical system. The optical fiber includes a distal side fiber portion in which the distal end is placed, and a proximal side fiber portion placed to a proximal direction side of the distal side fiber portion. Further, in the scanning endoscopic device, an actuator section placed to the distal direction side of the proximal side fiber portion is provided. When a drive current is supplied to the actuator section, the distal side fiber portion is driven, and the distal end of the optical fiber moves on a substantially flat surface perpendicular to a longitudinal axis. As a result, a position of the distal end of the optical fiber varies with time, and a collecting position (condensing position) of the irradiation light on the subject by the lens optical system varies with time. Furthermore, in the scanning endoscopic device, a light guide configured to receive reflection light reflected from the collecting position on the subject with time is provided. The reflection light received by the light guide is guided (led) to a light detection section, and a type and intensity of the reflection light are detected with time by the light detection section. As described above, in the scanning endoscopic device, the subject is scanned. Furthermore, based on a result of detection performed by the light detection section, an image of the subject is generated by an image processing section such as an image processing circuit.

BRIEF SUMMARY OF THE INVENTION

According to one aspect of the invention, a scanning endoscopic device which generates an image of a subject by scanning the subject, which includes that: an optical fiber which is extended along a longitudinal axis, and which includes a proximal side fiber portion, and a distal side fiber portion placed to a distal direction side of the proximal side fiber portion, the optical fiber being configured to allow irradiation light guided from the proximal side fiber portion to the distal side fiber portion to exit from a distal end thereof; a lens optical system which is arranged in a state that the irradiation light exiting from the distal end of the optical fiber is collected on the subject; an actuator section which is placed to the distal direction side of the proximal fiber portion, and which is configured to drive the distal side fiber portion in a state that the distal end of the optical fiber moves on a substantially flat surface perpendicular to the longitudinal axis; an outer envelope tube which is provided to an outer peripheral direction side of the optical fiber; and a light absorbing section which includes a black filling member filling a space between the proximal side fiber portion and the outer envelope tube in radial directions, and which is configured to absorb beam light having directivity in one direction.

According to one another aspect of the invention, a method of decreasing a directivity of beam light in a scanning endoscopic device which generates an image of a subject by scanning the subject, the method including that: allowing irradiation light guided to a distal side fiber portion from a proximal side fiber portion to exit from a distal end of an optical fiber, the optical fiber including the proximal side fiber portion, and the distal side fiber portion placed to the distal direction side of the proximal side fiber portion; collecting the irradiation light exiting from the distal end of the optical fiber on the subject by a lens optical system; driving the distal side fiber portion so that the distal end of the optical fiber moves on a substantially flat surface perpendicular to the longitudinal axis by using an actuator section placed to the distal direction side of the proximal side fiber portion, and changing a collecting position of the irradiation light on the subject formed by the lens optical system with time; receiving reflection light reflected from the collecting position on the subject with time, and leading the received reflection light from the distal direction toward a proximal direction by using a light guide extended at a part to an outer peripheral direction side of the optical fiber along the longitudinal axis; and absorbing a beam light by a light absorbing portion including a black filling member filling a space between an outer envelope tube and the proximal side fiber portion, the outer envelope tube being provided to the outer peripheral direction side of the optical fiber and the light guide, when the irradiation light is allowed to exit to the outside of the optical fiber from the proximal side fiber portion as the beam light having directivity in one direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a scanning endoscopic device according to a first embodiment of the present invention;

FIG. 2 is a block diagram schematically showing the scanning endoscopic device according to the first embodiment;

FIG. 5 is a cross-sectional view taken along a line V-V in FIG. 3;

FIG. 6 is a schematic view showing one example that a distal end of an optical fiber moves when a subject is scanned by using the scanning endoscopic device according to the first embodiment;

FIG. 7 is a cross-sectional view taken along a line VII-VII in FIG. 4;

FIG. 8 is a schematic view showing a manufacturing method of the insertion section in the scanning endoscopic device according to the first embodiment;

FIG. 9 is a cross-sectional view schematically showing a cross section perpendicular to a longitudinal axis which runs through a proximal side fiber portion of an insertion section according to a first modification;

FIG. 10 is a cross-sectional view schematically showing a configuration of one light guide of a scanning endoscopic device according to a second embodiment;

DETAILED DESCRIPTION OF THE INVENTION

First Embodiment

Figure 3:
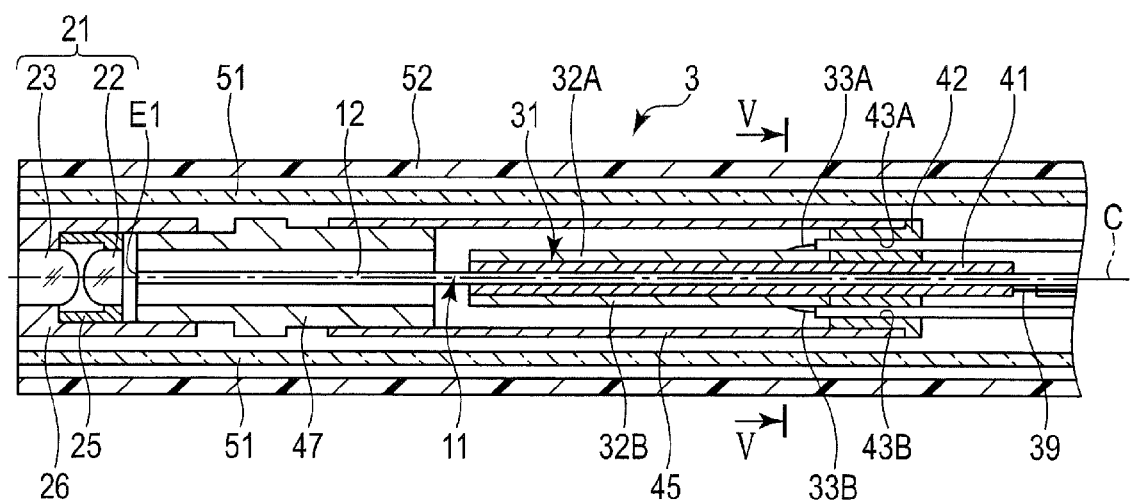
FIG. 3 is a cross-sectional view schematically showing a configuration of a distal end portion of an insertion section of a scanning endoscope according to the first embodiment.

A first embodiment according to the present invention will now be described with reference to FIG. 1 to FIG. 8.

FIG. 1 and FIG. 2 are views each showing a scanning endoscopic device 1 according to this embodiment. The scanning endoscopic device 1 is configured to scan a subject and generate an image of the subject. The scanning endoscopic device 1 has a longitudinal axis C. One of directions parallel to the longitudinal axis C is a distal direction (a direction of an arrow A1 in FIG. 1), and the other of the directions parallel to the longitudinal axis C is a proximal direction (a direction of an arrow A2 in FIG. 1).

As shown in FIG. 1 and FIG. 2, the scanning endoscopic device 1 includes a scanning endoscope 2. The scanning endoscope 2 includes an insertion section 3 extended along the longitudinal axis C, and a holding section 5 provided to the proximal direction side of the insertion section 3. One end of a universal cord 6 is connected to the holding section 5. The other end of the universal cord 6 is connected to a control unit 7. The control unit 7 is electrically connected to a monitor 8 which is a display section.

Figure 4:
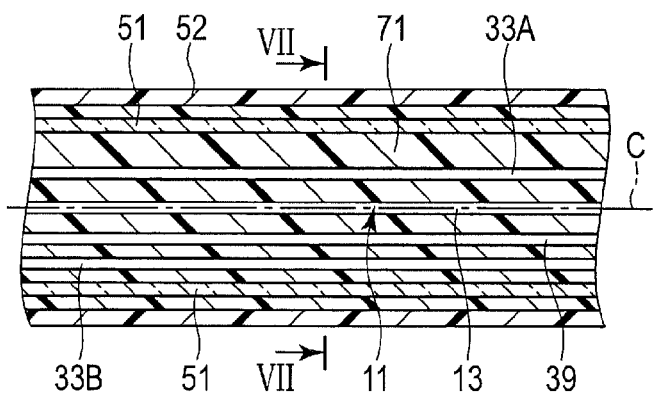
FIG. 4 is a cross-sectional view schematically showing a configuration of a part (region) to a proximal direction side of an actuator section in the insertion section of the scanning endoscope according to the first embodiment.

FIG. 3 is a view showing a configuration of a distal end portion of the insertion section 3 in the scanning endoscope 2. FIG. 4 is a view showing a configuration of a part (region) to the proximal direction side of an actuator section 31 (which will be described later) in the insertion section 3 of the scanning endoscope 2. As shown in FIG. 2 to FIG. 4, the scanning endoscopic device 1 includes an optical fiber 11 extended along the longitudinal axis C in the insertion section 3. The optical fiber 11 is optically connected to a light generation section 15 in the control unit 7 through an inside of the holding section 5 and an inside of the universal cord 6. Furthermore, the optical fiber 11 includes a distal side fiber portion 12 in which a distal end E1 of the optical fiber 11 is placed, and a proximal side fiber 13 placed to the proximal direction side of the distal side fiber portion 12.

A lens optical system 21 is provided to the distal direction side of the distal end E1 of the optical fiber 11. An optical axis of the lens optical system 21 coincides with the longitudinal axis C. The lens optical system 21 includes a first lens 22, and a second lens 23 which is provided to the distal direction side of the first lens 22. The first lens 22 is fixed to a first lens frame 25. Further, the second lens 23 is fixed to a second lens frame 26. The first lens frame 25 and the second lens frame 26 are made of a material with low light permeability such as a metal, and the first lens frame 25 is fixed to the second lens frame 26.

Furthermore, the actuator section 31 is provided to (in) the insertion section 3. The actuator section 31 is placed to the distal direction side of the proximal side fiber portion 13. FIG. 5 is a cross-sectional view taken along a line V-V in FIG. 3. The actuator section 31 includes piezoelectric elements 32A and 32B configured to generate ultrasonic vibration in X directions (directions of arrows X in FIG. 5) perpendicular to the longitudinal axis C, and piezoelectric elements 32C and 32D configured to ultrasonic vibration in Y directions (directions of arrows Y in FIG. 5) perpendicular to the longitudinal axis C and also perpendicular to the X directions. One end of each of electrical wiring lines 33A to 33D is connected to a corresponding one of the piezoelectric elements 32A to 32D. For example, one end of the electrical wiring line 33A is connected to the piezoelectric element 32A. The other end of each of the electrical wiring lines 33A to 33D is connected to a drive current supply section 35 in the control unit 7 through the inside of the holding section 5 and the inside of the universal cord 6.

The piezoelectric elements 32A to 32D are fixed to an outer peripheral portion of a ferrule 41. The ferrule 41 is made of a material with electric conductivity such as a metal. The distal side fiber portion 12 of the optical fiber 11 is attached to the ferrule 41 while being inserted through the ferrule 41. One end of an electrical wiring line 39 is connected to the ferrule 41. The other end of the electrical wiring line 39 is connected to the drive current supply section 35 of the control unit 7 through the inside of the holding section 5 and the inside of the universal cord 6. The electrical wiring line 39 serves as a ground line of the piezoelectric elements 32A to 32D. A drive current is supplied to the actuator section 31 through the electrical wiring lines 33A to 33D and 39.

A holder 42 is fixed to the ferrule 41. The ferrule 41 is electrically connected to the holder 42. Hole-shaped portions 43A to 43D pierced through (in) the holder 42 are formed in the holder 42 along the longitudinal axis C. Each of the electrical wiring lines 33A to 33D is inserted through a corresponding one of the hole-shaped portions 43A to 43D. For example, the electrical wiring line 33A is inserted through the hole-shaped portion 43A. It is to be noted that the electrical wiring lines 33A to 33D are prevented from electrically coming into contact with the holder 42.

A cylindrical connection member 45 is fixed to the holder 42. The actuator section 31 is accommodated in (inside) the connection member 45. Further, a cylindrical member 47 is fixed to the connection member 45. The distal end E1 of the distal side fiber portion 12 of the optical fiber 11 is accommodated in (inside) the cylindrical member 47. The cylindrical member 47 is fixed to the second lens frame 26. The connection member 45 and the cylindrical member 47 are made of a material with low light permeability such as a metal.

Light guides 51 are provided to an outer peripheral direction side of the optical fiber 11. Each light guide 51 is extended from a distal face of the insertion section 3 along the longitudinal axis C. Further, each light guide 51 is optically connected to a light detection section 55 in the control unit 7 through the inside of the holding section 5 and the inside of the universal cord 6. Each light guide 51 is placed to the outer peripheral direction side of the first lens frame 25, the second lens frame 26, the connection member 45, and the cylindrical member 47.

Furthermore, in the insertion section 3 of the scanning endoscope 2, an outer envelope tube 52 is provided to the outer peripheral direction side of the optical fiber 11 and the light guides 51. The outer envelope tube 52 forms part of an outer surface of the scanning endoscope 2. Moreover, in the insertion section 3, the light guides is located inside the outer envelope tube 52. The outer envelope tube 52 is made of a resin material and has a small wall thickness. Therefore, the outer envelope tube 52 has high light permeability. Additionally, since the wall thickness of the outer envelope tube 52 is small, a diameter of the insertion section 3 can be reduced.

As shown in FIG. 2, the control unit 7 includes an image processing section 61 such as an image processor configured to execute processing of generating images, and a central control section 62 configured to control the entire control unit 7. The image processing section 61 is electrically connected to the monitor 8. Further, the control unit 7 includes a power supply 63 such as a battery configured to supply electric power to the entire control unit 7, and a memory 65. The memory 65 is configured to record various kinds of specification information concerning the light generation section 15, the drive current supply section 35, and the light detection section 55, a program such as calculation processing executed in the central control section 62, and others. Furthermore, a memory 67 is provided in the holding section 5 of the scanning endoscope 2. The memory 67 is electrically connected to the central control section 62 of the control unit 7. Various kinds of specification information concerning the scanning endoscope 2 and others are recorded in the memory 67.

A description will now be given as to a configuration that scans the subject and generates an image of the subject by using the scanning endoscopic device 1. The light generation section 15 includes, e.g., three light sources 16A to 16C, and a multiplexing section 17. An Emission state of light from each of the light sources 16A to 16C is controlled by the central control section 62. The light sources 16A to 16C are configured to emit lights in wavelength bands different from each other. For example, the light source 16A emits light in a wavelength band of red (R), the light source 16B emits light in the wavelength band of green (G), and the light source 16C emits light in the wavelength band of blue (B). Moreover, the multiplexing section 17 is configured to combine the lights emitted from the light sources 16A to 16C, thereby forming white illumination light.

The combined irradiation light is guided (led) from the proximal direction toward the distal direction through the optical fiber 11. Additionally, the guided (led) irradiation light is allowed to exit from the distal end E1 of the optical fiber 11 (the distal side fiber portion 12). The irradiation light that has exited from the distal end E1 of the optical fiber 11 is collected (condensed) on the subject by the lens optical system 21. The irradiation light is collected on one collecting position (a spot) on the subject by the lens optical system 21.

The drive current supply section 35 includes a drive signal generation section 36, four digital/analog (D/A) conversion sections 37A to 37D, and an amplifier 38. The drive signal generation section 36 is configured to generate digital drive signals each of which generate ultrasonic vibration with use of a corresponding one of the piezoelectric elements 32A to 32D and configured to output each of them to the corresponding one of the D/A conversion sections 37A to 37D. For example, the digital drive signal that generates ultrasonic vibration in the piezoelectric element 32A is output to the D/A conversion section 37A. Output states of the respective digital drive signals from the drive signal generation section 36 are controlled by the central control section 62.

In each of the D/A conversion sections 37A to 37D, the corresponding digital drive signal is converted into drive current. Further, the drive current from each of the D/A conversion units 37A to 37D is amplified by the amplifier 38 and supplied to the corresponding one of the piezoelectric elements 32A to 32D through the corresponding one of the electric wiring lines 33A to 33D. For example, the drive current from the D/A conversion section 37A is supplied to the piezoelectric element 32A through the electric wiring line 33A. When the drive currents are supplied to the piezoelectric elements 32A and 32B, ultrasonic vibration in the X directions is generated. When the drive currents are supplied to the piezoelectric elements 32C and 32D, ultrasonic vibration in the Y directions is generated. The ultrasonic vibration generated by the piezoelectric elements 32A to 32D of the actuator section 31 is transmitted to the distal side fiber portion 12 of the optical fiber 11. As a result, the distal side fiber portion 12 is driven.

When the distal side fiber portion 12 is driven, the distal end E1 of the optical fiber 11 (the distal side fiber portion 12) moves on a substantially flat surface perpendicular to the longitudinal axis C. A moving state of the distal end E1 of the optical fiber 11 is adjusted by controlling output of each of the digital drive signals in the drive signal generation section 36. As an example, the distal end E1 of the optical fiber 11 is adjusted to helically move on the substantially flat surface perpendicular to the longitudinal axis C as shown in FIG. 6. When the distal end E1 of the optical fiber 11 moves, the position in which the irradiation light exits from the distal end E1 of the optical fiber 11 varies with time. Therefore, a collecting position of the irradiation light on the subject formed by the lens optical system 21 varies with time. Here, moving on the substantially flat surface is not necessarily strictly restricted to movement of the distal end E1 of the optical fiber 11 on the flat surface, but it means that a moving length of the distal end E1 of the optical fiber 11 in directions parallel to the longitudinal axis C is small so that the distal end E1 can be considered as moving on a flat surface.

The irradiation light applied to the collecting position (condensing position) on the subject is reflected on the collecting position. Further, each light guide 51 receives the reflected light reflected on the collecting position with time. The reflected light received by each light guide 51 is guided (led) by each light guide 51 from the distal direction to the proximal direction. Furthermore, the light is guided to the light detection section 55 by each light guide 51.

The light detection section 55 includes a demultiplexing section 56, three light intensity detection sections 57A to 57C, and three analog/digital (A/D) conversion sections 58A to 58C. The demultiplexing section 56 is, e.g., a dichroic mirror, and it is configured to divide the reflected light guided by each light guide 51 into lights in three wavelength bands different from each other. For example, the guided reflected light is separated into first separated light in a wavelength band of red (R), second separated light in a wavelength band of green (G), and third separated light in a wavelength band of blue (B), respectively.

Moreover, the first separated light is guided to the light intensity detection section 57A, and an intensity of the first separated light is detected by the light intensity detection section 57A. Additionally, a current that is a physical quantity based on the intensity of the first separated light is output to the A/D conversion section 58A, and the current is converted into a digital signal by the A/D conversion section 58A. Further, the digital signal indicative of information based on the intensity of the first separated light is transmitted to the central control section 62. In the light intensity detection section 57B and the A/D conversion section 58B, like the light intensity detection section 57A and the A/D conversion section 58A, an intensity of the second separated light is detected. Furthermore, a digital signal indicative of information based on the intensity of the second separated light is transmitted to the central control section 62. Moreover, in the light intensity detection section 57C and the A/D conversion section 58C, like the light intensity detection section 57A and the A/D conversion section 58A, an intensity of the third separated light is detected. Additionally, a digital signal indicative of information based on the intensity of the third separated light is transmitted to the central control section 62. As described above, the light detection section 55 is configured to detect a type and intensity of the reflected light guided (led) by each light guide 51 with time.

That is, in the case of observing the subject by using the scanning endoscopic device 1, the collecting position of the irradiation light on the subject varies with time. Further, the light detection section 55 sequentially detects a type and intensity of the reflected light reflected from the collecting position which varies with time. As a result, scanning of the subject is performed.

The central control section 62 includes a collecting position detection section 69 configured to detect the collecting position of the irradiation light on the subject, the collecting position being formed by the lens optical system 21, with time. The collecting position detection section 69 detects the collecting position of the irradiation light on the subject based on specification information of the scanning endoscope 2, specification information of the control unit 7, and each of the digital drive signals from the drive signal generation section 36. That is, the collecting position (condensing position) of the irradiation light on the subject is detected based on each of the drive currents supplied from the drive current supply section 35 to the actuator section 31.

The image processing section 61 generates an image of the subject based on the collecting position detected with time and the type and the intensity of the reflected light detected with time. Further, the generated image is displayed in the monitor 8.

FIG. 7 is a cross-sectional view taken along a line VII-VII in FIG. 4. As shown in FIG. 4 and FIG. 7, in the insertion section 3, a space between the proximal side fiber portion 13 of the optical fiber 11 and the outer envelope tube 52 in the radial directions is filled with a filling member 71. A part (region) to the proximal direction side of the actuator section 31 in the insertion section 3 is filled with the filling member 71. The filling member 71 is black and made of a resin material such as silicone. The filling member 71 is configured to absorb beam light having directivity in one direction. That is, the filling member 71 serves as a light absorbing section configured to absorb the beam light. When the beam light is absorbed, the directivity of the beam light having the directivity in the one direction is reduced. That is, the filling member 71 serves as a directivity decreasing section configured to decrease the directivity of the beam light.

FIG. 8 is a view showing a method of manufacturing the insertion section 3. As shown in FIG. 8, at the time of manufacturing the insertion section 3, the built-in members, e.g., the optical fiber 11, the lens optical system 21, the actuator section 31, the light guides 51, and others are inserted into the outer envelope tube 52 by using a jig 72. At this time, the built-in members, e.g., the optical fiber 11 and others move from the proximal direction toward the distal direction inside the outer envelope tube 52 by using the jig 72. Furthermore, the space between the proximal side fiber portion 13 and the envelope coat tube 52 in the radial directions is filled with the filling member 71 while inserting the built-in members into the outer envelope tube 52. Filling with the filling member 71 is carried out with use of a syringe 73.

A function of the scanning endoscopic device 1 will now be described. At the time of scanning the subject by using the scanning endoscopic device 1, the proximal side fiber portion 13 of the optical fiber 11 may be damaged. In this case, the irradiation light exits from a damaged position of the proximal side fiber portion 13 as beam light having directivity in one direction. Here, the space between the proximal side fiber portion 13 and the outer envelope tube 52 in the radial directions is filled with the filling member 71. Therefore, even if the beam light having the directivity in the one direction is allowed to exit from the proximal side fiber portion 13, the beam light is absorbed by the filling member (the light absorbing section) 71. As a result, the directivity of the beam light is decreased. When the directivity of the beam light is decreased by the filling member (a directivity decreasing section) 71, the beam light having high intensity can be prevented from exiting toward the outer peripheral direction side of the outer envelope tube 52. Moreover, when the filling member 71 is provided, the wall thickness of the outer envelope tube 52 does not have to be increased.

As described above, in the scanning endoscopic device 1 according to this embodiment, the directivity of the beam light exiting from the proximal side fiber portion 13 can be effectively reduced without increasing the wall thickness of the outer envelope tube 52.

Modification of First Embodiment

It is to be noted that, in the first embodiment, although the beam light is absorbed by the filling member 71, the present invention is not restricted thereto. For example, as a first modification, the filling member 71 does not have to be provided as depicted in FIG. 9. FIG. 9 is a view showing a cross section perpendicular to the longitudinal axis C running through the proximal side fiber portion 13 of the insertion section 3. In this modification, like the first embodiment, the optical fiber 11, the electrical wiring lines 33A to 33D and 39, and the light guides 51 are provided.

The electrical wiring lines 33A to 33D and 39 and the light guides 51 are densely arranged between the proximal side fiber portion 13 of the optical fiber 11 and the outer envelope tube 52 in the radial directions. In this modification, a coating portion 75 is formed on an outer surface of each light guide 51 by a coating processing. Additionally, each of the electrical wiring lines 33A to 33D and 39 is covered with a covering member 76. The coating portion 75 and the covering member 76 are black.

In this modification, when the irradiation light is allowed to exit from a damaged position of the proximal side fiber portion 13 as beam light having directivity in one direction, the beam light is absorbed by the coating portions 75 and the covering members 76. That is, each of the coating portions 75 and the covering members 76 functions as a light absorbing section configured to absorb the beam light. When the beam light is absorbed, the directivity of the beam light having the directivity in the one direction is decreased. That is, each of the coating portions 75 and the covering members 76 serves as a directivity decreasing section configured to decrease the directivity of the beam light. The coating portions 75 and the covering members 76 are provided between the proximal side fiber portion 13 and the outer envelope tube 52 in the radial directions.

Second Embodiment

Figure 11:
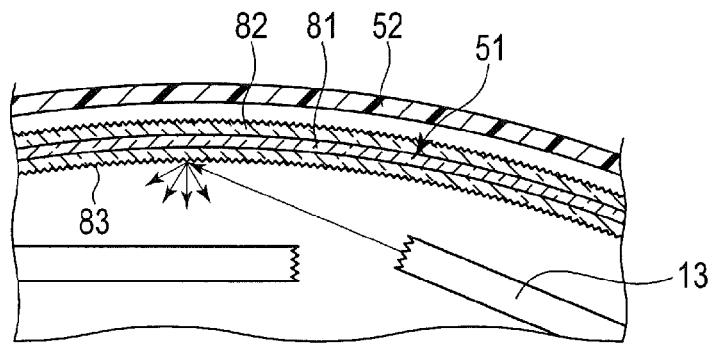
FIG. 11 is a schematic view for explaining a function of an uneven surface portion of the light guide of the scanning endoscopic device according to the second embodiment.

A second embodiment according to the present invention will now be described with reference to FIG. 10 and FIG. 11. It is to be noted that like reference numerals denote the same parts or parts having the same functions as those in the first embodiment, and a detailed description thereof will be omitted.

In this embodiment, like the first embodiment, an optical fiber 11, an actuator section 31, electrical wiring lines 33A to 33D and 39, and light guides 51 are provided. FIG. 10 is a view showing a configuration of one light guide 51. It is to be noted that FIG. 10 shows the configuration of one light guide 51 alone, but the other light guides 51 have the same configuration.

As shown in FIG. 10, each light guide 51 includes a core 81 and a clad 82. An uneven surface portion 83 having an uneven shape is formed on an outer surface of the clad 82 of each light guide 51. The uneven surface portion 83 is formed by attaching glass powder made of the same material as the clad 82 to the outer surface of the clad 82.

In the case of scanning a subject by using a scanning endoscopic device 1 as described above, a proximal side fiber portion 13 of the optical fiber 11 may be damaged in some circumstances. In this case, irradiation light is allowed to exit from a damaged position of the proximal side fiber portion 13 as beam light having directivity in one direction. FIG. 11 is a view for explaining a function of the uneven surface portion 83. In this modification, the light guides 51 are provided between the proximal side fiber portion 13 and the outer envelope tube 52 in radial directions, and the uneven surface portion 83 is formed on an outer surface of each light guide 51. Therefore, as shown in FIG. 11, even if beam light having directivity in one direction is allowed to exit from the proximal side fiber portion 13, the beam light is reflected in a diffused manner by the uneven surface portion 83, and the beam light is scattered. That is, the uneven surface portion 83 serves as a light scattering section configured to scatter the beam light. When the beam light is scattered, the directivity of the beam light having the directivity in the one direction is reduced. That is, the uneven surface portion 83 functions as a directivity decreasing section configured to decrease the directivity of the beam light.

When the directivity of the beam light is reduced by the uneven surface portion 83, the high-intensity beam light is effectively prevented from exiting toward the outer peripheral direction side of the outer envelope tube 52. Additionally, when the uneven surface portion 83 is provided, a wall thickness of the outer envelope tube 52 does not have to be increased. As described above, in the scanning endoscopic device 1 according to this embodiment, the directivity of the beam light exiting from the proximal side fiber portion 13 can be effectively reduced without increasing the wall thickness of the outer envelope tube 52.

Modification of Second Embodiment

Figure 12:
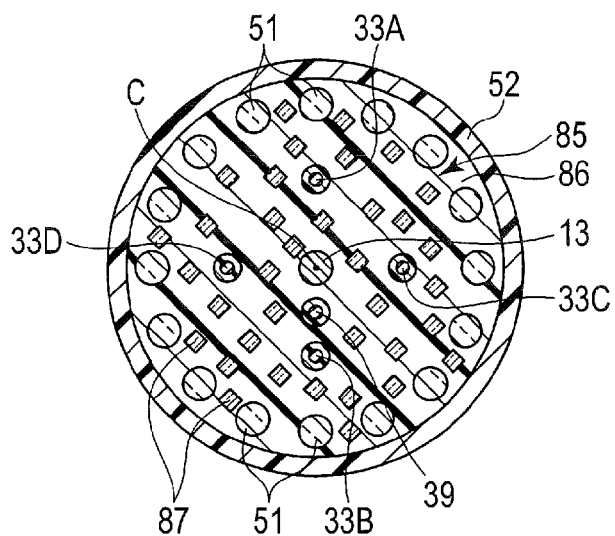
FIG. 12 is a cross-sectional view schematically showing a cross section perpendicular to a longitudinal axis which runs through a proximal side fiber portion of an insertion section according to a second modification.

It is to be noted that, in the second embodiment, although beam light is scattered by the uneven surface portion 83, the present invention is not restricted thereto. For example, as a second modification, the uneven surface portion 83 does not have to be provided as shown in FIG. 12. FIG. 12 is a view showing a cross section perpendicular to a longitudinal axis C running through a proximal side fiber portion 13 of an insertion section 3. In this modification, like the second embodiment, the optical fiber 11 and the light guides 51 are provided.

In this modification, a space between the proximal side fiber portion 13 of the optical fiber and the outer envelope tube 52 in the radial directions is filled with a filling member 85. The filling member 85 is formed by mixing a reflection member 87 such as glass powder or metal powder in a resin member 86 such as silicone. At the time of manufacturing the insertion section 3, like the filling member 71 in the first embodiment, filling with the filling member 85 is carried out (see FIG. 8).

In this modification, when irradiation light is allowed to exit from a damaged position of the proximal side fiber portion 13 as beam light having directivity in one direction, the beam light is scattered by the reflection member 87. That is, the reflection member 87 serves as a light scattering section configured to scatter the beam light. When the beam light is scattered, the directivity of the beam light having the directivity in one direction is reduced. That is, the reflection member 87 functions as a directivity decreasing section configured to reduce the directivity of the beam light.

Moreover, when the resin member 86 of the filling member 85 is black, like the filling member 71 according to the first embodiment, the beam light is absorbed by the resin member 86. In this case, the resin member 86 serves as a light absorbing section and a directivity decreasing section.

Figure 13:
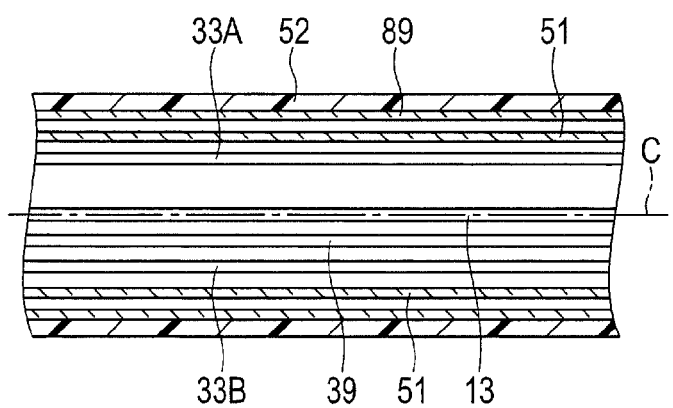
FIG. 13 is a cross-sectional view schematically showing a configuration of a part (region) to a proximal direction side of an actuator section in an insertion section of a scanning endoscope according to a third modification.

Additionally, in a third modification shown in FIG. 13, likewise, the uneven surface portion 83 is not provided. FIG. 13 is a view showing a cross section that is parallel to the longitudinal axis C running through the proximal side fiber portion 13 of the insertion unit 3. In this modification, a scattering layer 89 is provided on an inner peripheral portion of the outer envelope tube 52. The scattering layer 89 is formed by performing, e.g., a sand surface processing with respect to the inner peripheral portion of the outer envelope tube 52 or applying scattering fine particles to the inner peripheral portion of the outer envelope tube 52. The scattering layer 89 is placed between the proximal side fiber portion 13 of the optical fiber 11 and the outer envelope tube 52 in the radial directions.

In this modification, when irradiation light is allowed to exit from a damaged position of the proximal side fiber portion 13 as beam light having directivity in one direction, the beam light is scattered by the scattering layer 89. That is, the scattering layer 89 functions as a light scattering section configured to scatter the beam light. When the beam light is scattered, the directivity of the beam light having the directivity in the one direction is decreased. That is, the scattering layer 89 serves as a directivity decreasing section configured to reduce the directivity of the beam light.

Third Embodiment

A third embodiment according to the present invention will now be described with reference to FIG. 14. It is to be noted that like reference numerals denote the same parts or parts having the same functions as those in the first embodiment or the second embodiment, and a description thereof will be omitted.

Figure 14:
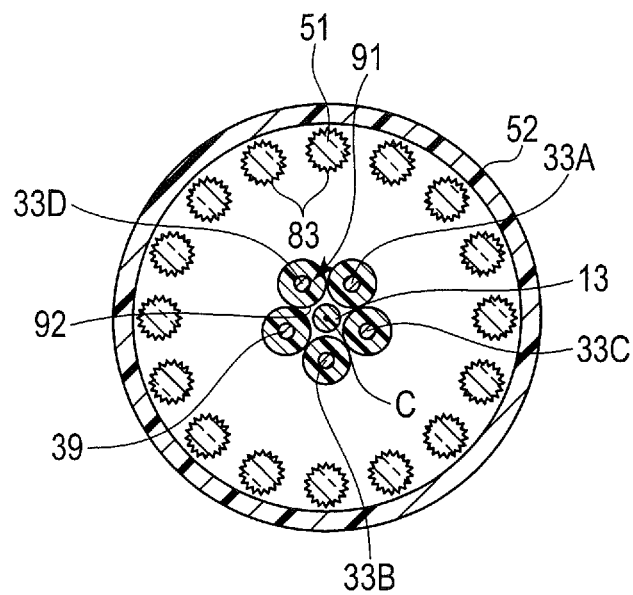
FIG. 14 is a cross-sectional view schematically showing a cross section perpendicular to a longitudinal axis which runs through a proximal side fiber portion of an insertion section according to a third embodiment.

FIG. 14 is a view showing a cross section perpendicular to a longitudinal axis C running through a proximal side fiber portion 13 of an insertion section 3. As shown in FIG. 14, in this embodiment, like the first embodiment, an optical fiber 11, an actuator section 31, electrical wiring lines 33A to 33D and 39, and light guides 51 are provided. Further, like the second embodiment, an uneven surface portion 83 is formed on an outer surface of each light guide 51.

In this embodiment, the electrical wiring lines 33A to 33D and 39 are placed to the inner peripheral direction side of the light guides 51. The electrical wiring lines 33A to 33D and 39 are cylindrical braided, thereby forming a wiring cylindrical portion 91. As a result, the proximal side fiber portion 13 is surrounded by the wiring cylindrical portion 91 (the electrical wiring lines 33A to 33D and 39).

A movement regulating portion 92 is provided on an inner peripheral portion of the wiring cylindrical portion 91. Since the proximal side fiber portion 13 is surrounded by the electrical wiring lines 33A to 33D and 39, the movement regulating portion 92 is provided to the outer peripheral direction side of the proximal side fiber portion with surrounding the proximal side fiber portion 13. The movement regulating portion 92 is configured to regulate a movement range of the proximal side fiber portion 13 in the radial directions. That is, the movement of the proximal side fiber portion 13 toward the outer peripheral direction side of the electrical wiring lines 33A to 33D and 39 is regulated.

The movement regulating portion 92 is placed to the inner peripheral direction side of an outer envelope tube 52. Therefore, even if the proximal side fiber portion 13 is damaged, the movement of a damaged position of the proximal side fiber portion 13 toward the outer peripheral direction side of the movement regulating portion 92 (the electrical wiring lines 33A to 33D and 39) is regulated. Therefore, the movement of the damaged position of the proximal side fiber portion 13 toward the outer peripheral direction side of the outer envelope tube 52 is prevented. As a result, high-intensity beam light can be further effectively prevented from exiting toward the outer peripheral direction side of the outer envelope tube 52.

Reference Example

Figure 15:
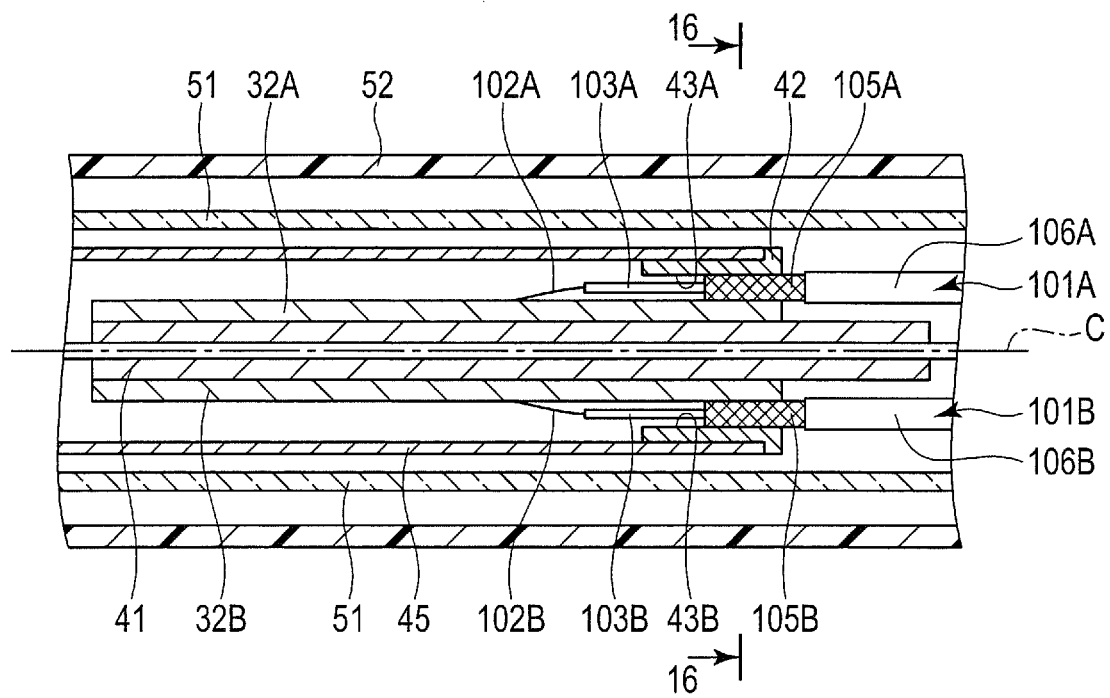
FIG. 15 is a cross-sectional view schematically showing a configuration of an insertion section near an actuator section according to a first reference example.
Figure 16:
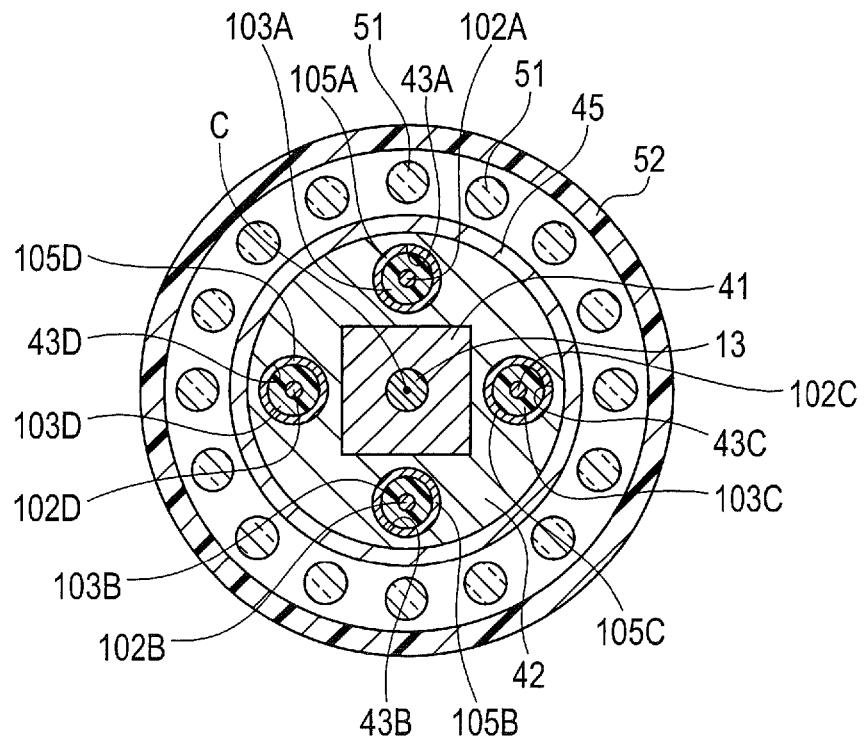
FIG. 16 is a cross-sectional view taken along a line 16-16 in FIG. 15.

Furthermore, in a first reference example shown in FIG. 15 and FIG. 16, the electrical wiring lines 33A to 33D and 39 are not provided. In place of these members, four shield lines 101A to 101D are provided. A proximal end of each of the shield lines 101A to 101D is connected to the drive current supply section 35 of the control unit 7 through an inside of the holding section 5 and an inside of the universal cord 6.

The shield line 101A includes a core wire 102A, a core wire covering portion 103A covering the core wire 102A, a shield 105A covering the core covering portion 103A, and a shield covering portion 106A covering the shield 105A. Each of the core wire 102A and the shield 105A is made of a conductive material. Each of the core wire covering portion 103A and the shield covering portion 106A is made of an insulating material. Like the shield line 101A, each of the other shield lines 101B to 101D includes a core wire 102B, 102C or 102D, a core wire covering portions 103B, 103C or 103D, a shield 105B, 105C or 105D, and a shield covering portion 106B, 106C or 106D.

Each of the core wires 102A to 102D and each of the core wire covering portions 103A to 103D are inserted through a corresponding one of hole-shaped portions 43A to 43D in a holder 42. For example, the core wire 102A and the core wire covering portion 103A are inserted through the hole-shaped portion 43A. Furthermore, a distal end of each of the core wires 102A to 102D is connected to a corresponding one of piezoelectric elements 32A to 32D. For example, a distal end of the core wire 102A is connected to the piezoelectric element 32A.

Each of the shields 105A to 105D is inserted into the corresponding one of the hole-shaped portions 43A to 43D. Moreover, a distal end of each of the shields 105A to 105D is connected to the holder 42 in the corresponding one of the hole-shaped portions 43A to 43D. A ferrule 41 is electrically connected to the holder 42. Therefore, in this reference example, the shields 105A to 105D serve as ground lines of the piezoelectric elements 32A to 32D. As described above, when the shield lines 101A to 101D are used for supplying a drive current to the actuator section 31, electromagnetic compatibility (EMC) is improved as compared with a case where the electrical wiring lines 33A to 33D and 39 are used.

Figure 17:
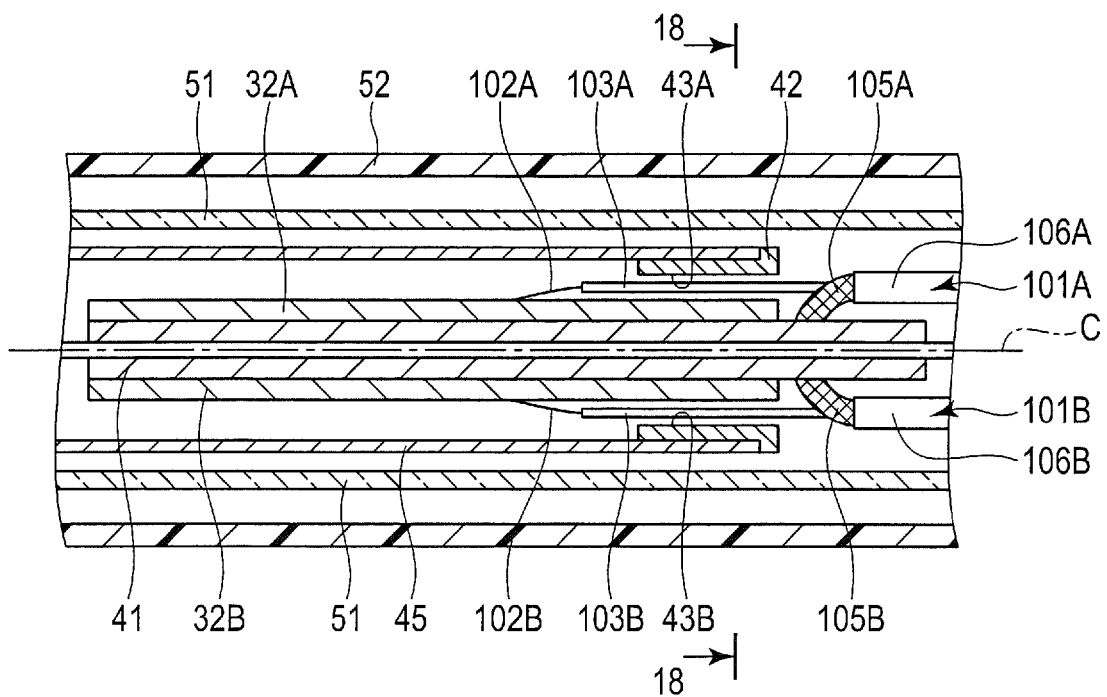
FIG. 17 is a cross-sectional view schematically showing a configuration of an insertion section near an actuator section according to a second reference example.
Figure 18:
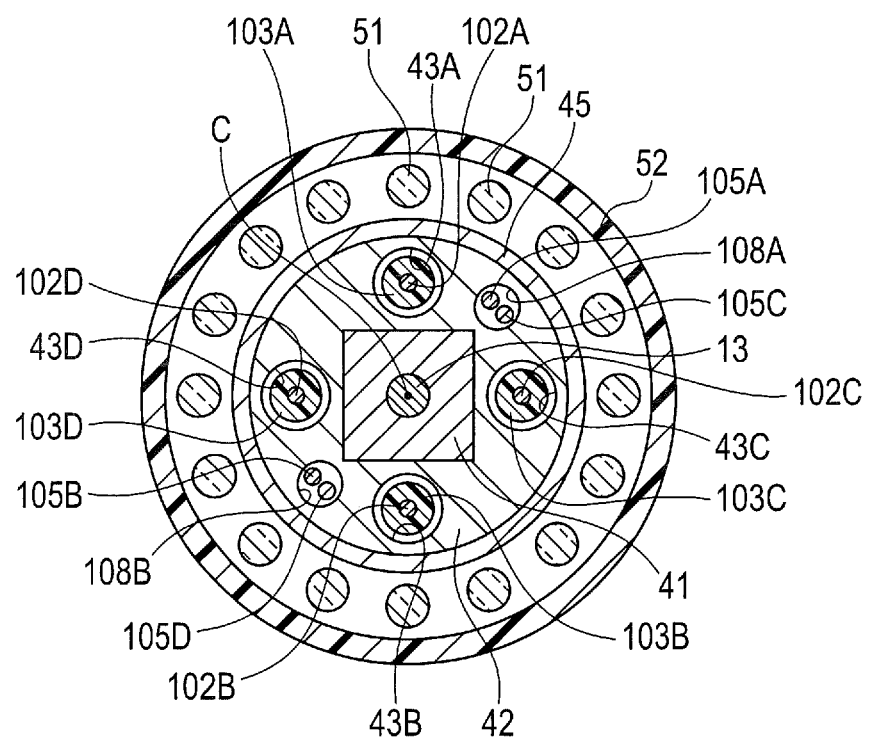
FIG. 18 is a cross-sectional view taken along a line 18-18 in FIG. 17.

Additionally, as a configuration using the shield lines 101A to 101D in place of the electrical wiring lines 33A to 33D and 39, there is a second reference example shown in FIG. 17 and FIG. 18. In this reference example, like the first reference example, each of the core wires 102A to 102D and each of the core wire covering portions 103A to 103D are inserted through the corresponding one of the hole-shaped portions 43A to 43D in the holder 42. Further, a distal end of each of the core wires 102A to 102D is connected to the corresponding one of the piezoelectric elements 32A to 32D.

In this reference example, two hole-shaped portions 108A and 108B are provided in the holder 42 in addition to the hole-shaped portions 43A to 43D. The hole-shaped portion 108A is placed between the hole-shaped portion 43A and the hole-shaped portion 43C in periaxial directions of the longitudinal axis. The shields 105A and 105C are inserted into the hole-shaped portion 108A. Furthermore, a distal end of each of the shields 105A and 105C is connected to the holder 42 in the hole-shaped portion 108A. Moreover, the hole-shaped portion 108B is placed between the hole-shaped portion 43B and the hole-shaped portion 43D in the periaxial directions of the longitudinal direction. The shields 105B and 105D are inserted into the hole-shaped portion 108B. Additionally, a distal end of each of the shields 105B and 105D is connected to the holder 42 in the hole-shaped portion 108B.

In this reference example, the shields 105A to 105D serve as ground lines of the piezoelectric elements 32A to 32D. As described above, when the shield lines 101A to 101D are used for supplying a drive current to the actuator section 31, the electromagnetic compatibility (EMC) is improved as compared with the case where the electric wiring lines 33A to 33D and 39 are used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A scanning endoscopic device which generates an image of a subject by scanning the subject, comprising:
    an optical fiber which is extended along a longitudinal axis, and which includes a proximal side fiber portion, and a distal side fiber portion placed to a distal direction side of the proximal side fiber portion, the optical fiber being configured to allow irradiation light guided from the proximal side fiber portion to the distal side fiber portion to exit from a distal end thereof;
    a lens optical system which is arranged in a state that the irradiation light exiting from the distal end of the optical fiber is collected on the subject;
    an actuator section which is placed to the distal direction side of the proximal fiber portion, and which is configured to drive the distal side fiber portion in a state that the distal end of the optical fiber moves on a substantially flat surface perpendicular to the longitudinal axis;
    an outer envelope tube which is provided to an outer peripheral direction side of the optical fiber;
    a light absorbing section which includes a black filling member filling a space between the proximal side fiber portion and the outer envelope tube in radial directions, and which is configured to absorb beam light having directivity in one direction; and
    a light scattering section which is provided between the proximal side fiber portion and the outer envelope tube in the radial directions, and which is configured to scatter the beam light.

2. The device according to claim 1, wherein the filling member fills a part to a proximal direction side of the actuator section.

3. The device according to claim 1, wherein the light scattering section includes a powdered reflection member contained in the filling member.

4. The device according to claim 1, further comprising a light guide which is extended along the longitudinal axis between the optical fiber and the outer envelope tube in the radial directions, and which is configured to receive reflection light reflected from a collecting position of the irradiation light on the subject with time, the light guide being configured to guide the received reflected light from the distal direction toward a proximal direction.

5. The device according to claim 1, further comprising a movement regulating portion which is provided to the outer peripheral direction side of the proximal side fiber portion while surrounding the proximal side fiber portion, and which is configured to regulate a movement range of the proximal side fiber portion in the radial directions.

6. The device according to claim 5, further comprising electrical wiring lines which are extended along the longitudinal axis between the proximal side fiber portion and the outer envelope tube in the radial directions, a current being configured to be supplied to the actuator section through each of the electrical wiring lines,
    wherein the movement regulating portion is formed by surrounding the proximal side fiber portion with the electrical wiring lines, and is configured to regulate movement of the proximal side fiber portion toward the outer peripheral direction side of the electrical wiring lines.

* * * * *